United States Patent
Wahlig et al.

(10) Patent No.: US 6,755,563 B2
(45) Date of Patent: Jun. 29, 2004

(54) PREPARATION AND APPLICATION DEVICE FOR MATERIALS TO BE PREPARED AS A PASTE-LIKE FLOWABLE MASS, ESPECIALLY BONE CEMENT

(75) Inventors: Helmut Wahlig, Darmstadt (DE); Elvira Dingeldein, Dreieich (DE); Christoph Sattig, Rodgau (DE); Edgar Wüst, Dieburg (DE)

(73) Assignee: Coripharm Medizinprodukte GmbH & Co. KG, Dieburg (DE)

( * ) Notice: Subject to any disclaimer, the term of this patent is extended or adjusted under 35 U.S.C. 154(b) by 56 days.

(21) Appl. No.: 10/275,043
(22) PCT Filed: Mar. 21, 2001
(86) PCT No.: PCT/EP01/03236
§ 371 (c)(1), (2), (4) Date: Oct. 31, 2002
(87) PCT Pub. No.: WO01/85070
PCT Pub. Date: Nov. 15, 2001

(65) Prior Publication Data
US 2003/0075564 A1 Apr. 24, 2003

(30) Foreign Application Priority Data
May 5, 2000 (DE) .......................................... 200081039

(51) Int. Cl.[7] .............................. B01F 13/00; A61F 2/46
(52) U.S. Cl. ........................ 366/139; 366/256; 366/347
(58) Field of Search ................................ 366/139, 256, 366/255, 242, 129, 130, 347, 189

(56) References Cited

U.S. PATENT DOCUMENTS

| | | | |
|---|---|---|---|
| 4,874,368 A | 10/1989 | Miller et al. | 604/82 |
| 4,961,647 A | 10/1990 | Coutts et al. | 366/139 |
| 4,973,168 A | 11/1990 | Chan | 366/139 |
| 5,100,241 A | 3/1992 | Chan | 366/139 |
| 5,114,240 A | 5/1992 | Kindt-Larsen et al. | 366/129 |
| 5,193,907 A | 3/1993 | Faccioli et al. | 366/130 |
| 5,252,301 A | 10/1993 | Nilson et al. | 366/139 |
| 5,328,262 A | 7/1994 | Lidgren et al. | 366/139 |

(List continued on next page.)

FOREIGN PATENT DOCUMENTS

| | | |
|---|---|---|
| DE | 84 20 774.4 | 10/1985 |
| DE | 34 25 566 A1 | 1/1986 |

(List continued on next page.)

*Primary Examiner*—Tony G. Soohoo
(74) *Attorney, Agent, or Firm*—Norris McLaughlin & Marcus P.A.

(57) ABSTRACT

The invention relates to a preparation and application device for materials which are to be prepared as a paste-like, flowable mass from at least one powder or granulate component and one liquid component, especially bone cement, with an elongated mixing cylinder for receiving the components to be mixed, comprising in one end region a sealable through-opening that can optionally be provided with a discharge unit for the paste-like material to be prepared, and a piston which can be inserted into the other, opposite, open end. The piston is displaceable in the cylinder and seals against the inner wall of the cylinder. The piston is penetrated by an elongated mixing shaft sealed against the piston, and a mixing mechanism is disposed at the cylinder inside-end of the mixing shaft and a handle disposed at the cylinder outside-end of the mixing shaft. The open end of the cylinder located opposite the through-opening and receiving the piston is additionally provided with a removable sealing cap that can be secured on and removed from the cylinder or piston and has a through-opening for the mixing shaft. The piston on the side of the sealing cap has a vacuum fitting adapted for connection to a vacuum source, which can produce a vacuum in the interior of the cylinder through a passageway provided in the piston. The sealing cap includes a through-opening through which the vacuum line that is connected to the vacuum source can be connected to the vacuum fitting in the piston.

13 Claims, 4 Drawing Sheets

U.S. PATENT DOCUMENTS

| | | | |
|---|---|---|---|
| 5,435,645 A | 7/1995 | Faccioli et al. | 366/130 |
| 5,501,520 A | 3/1996 | Lidgren et al. | 366/139 |
| 5,586,821 A | 12/1996 | Bonitati et al. | 366/139 |
| 5,624,184 A | 4/1997 | Chan | 366/139 |
| 5,779,356 A | 7/1998 | Chan | 366/139 |
| 6,017,349 A | 1/2000 | Heller et al. | 366/139 |

FOREIGN PATENT DOCUMENTS

| | | |
|---|---|---|
| DE | 36 09 672 A1 | 9/1987 |
| DE | 37 01 190 A1 | 7/1988 |
| DE | 40 22 986 A1 | 1/1992 |
| DE | 42 43 877 C2 | 7/1994 |
| DE | 195 00 782 A1 | 7/1996 |
| EP | 0 412 198 A1 | 2/1991 |

PREPARATION AND APPLICATION DEVICE FOR MATERIALS TO BE PREPARED AS A PASTE-LIKE FLOWABLE MASS, ESPECIALLY BONE CEMENT

BACKGROUND

Bone cement is typically prepared from a polymer powder component and a liquid monomer component by thorough mixing to form a paste-like flowable mass which then hardens and/or binds after being introduced, for example, into the medullary channel of the femur of a patient for the purpose of anchoring the shaft of a hip replacement prosthesis, thereby ensuring a permanent load-bearing attachment of the prosthesis in the femur. It is known since many years that the mechanical stability of bone cements is substantially reduced by greater and smaller air inclusions which are introduced into the resulting cement matrix in particular when the cement components are mixed. The air bubbles enclosed in the cement produce pores which can lead to the formation of fissures and gaps in the cement when subsequently stressed by the prosthesis. This can prematurely destroy the cement jacket surrounding the prosthesis which in turn can loosen the prosthesis, necessitating its removal. Experimental and clinical studies have shown that substantially air-free and hence also pore-free cements contribute to an increased fatigue resistance and thereby extend the lifetime of the endoprosthesis. Mixing systems for bone cement have been developed, whereby the mixing process is carried out under vacuum. For example, mixing vessels have been developed, whereby the vessel is closed off after the components are introduced, so that monomer vapors cannot escape during the mixing process. In other systems, the mixing process is carried out under reduced atmospheric pressure after the mixing vessel is filled. In this case, the monomer vapors are typically suctioned off with a vacuum pump and trapped in a charcoal filter. Air inclusions during mixing can be significantly reduced by reducing the pressure, which significantly increases the stability of the bone cement and therefore also the lifetime of an endoprosthesis anchored with bone cement in the bone.

SUMMARY OF INVENTION

It is therefore an object of the invention to provide a device for preparing, i.e. thoroughly mixing, the components of an exemplary bone cement under vacuum, wherein the device is comparatively simpler than conventional systems and enables application of completely mixed bone cement in the designated attachment region while the mixed bone cement is still in a flowable paste-like state. Vacuum is applied only during the mixing process of the bone cement component, whereas the actual application is carried out with the device after the device has been vented, i.e., under atmospheric pressure.

Based on a device of the aforedescribed type, the object is solved by the invention in that the sealing cap, which can be placed over the edge of the open end of the cylinder, is movably connected to at least one elongated locking element which can be inserted through corresponding recesses provided in the edge region of the cylinder and through corresponding openings provided in the piston. When the locking element(s) is/are inserted, it/they hold(s) the sealing cap and the cylinder on or in the open end region of the cylinder. Locking the piston with the sealing cap ensures that the piston, which is mounted on the cylinder together with the sealing cap after the material components to be mixed have been filled in, is secured in the upper end position due to the fact that the cap and the piston interlock when the mixing mechanism is operated by simultaneously displacing and rotating the mixing shaft. Mixing takes place in vacuum, as required, which is introduced by the vacuum source via the vacuum fitting.

According to a preferred embodiment of the invention, the locking element(s) is/are formed as elongated flat locking bracket(s), with the sealing cap pivotally joined with the locking bracket(s). When the sealing cap and the locking bracket(s) are formed as injection molded plastic parts, the locking bracket(s) can be hingedly connected to the sealing cap via an integrally formed film hinge. According to a preferred embodiment of the invention, two mutually parallel locking brackets are provided that have flat side surfaces located in a plane.

According to another advantageous embodiment of the invention, the locking brackets are pre-mounted in a corresponding through-opening of the piston, which through-opening penetrates the piston perpendicular to the piston's longitudinal center axis and is complementary to the cross-section of the locking brackets. Open recesses which have a narrowed mouth adapted to receive the locking brackets are provided in the end region of the open cylinder. When the piston is in the intended locked position, the locking brackets can be elastically pressed together in the transverse direction in a region located at the open end of the cylinder. Accordingly, the piston held by the locking brackets together with the sealing cap can be secured in the open end by elastic compression in the transverse direction.

Advantageously, the locking brackets can be elastically compressed in the transverse direction in the region of the recesses near the edge of the cylinder as a result of elongated through-holes disposed in the locking brackets in a region that in the intended locking position is located in the recesses of the cylinder, wherein the through-holes permit a relative deformation of the remaining edge regions.

The piston, the mixing shaft which movably penetrates the piston and is provided on its, cylinder-interior end with the mixing mechanism and on the exterior end with a handle, as well as the sealing cap that is penetrated by the mixing shaft, together with the latching brackets that are pre-mounted in the through-openings in the piston, are pre-mounted in the form of an assembly that can be inserted in the open end of the cylinder and locked by engaging the locking brackets in the recesses disposed in the edge region of the open end of the cylinder. The pre-mounted assembly can be inserted into the cylinder as a unit—after the cylinder has been filled with the bone cement components—, whereby the piston and the sealing cap interlock in the open edge region. After interlocking, the connecting line to the vacuum source can be connected to the vacuum connection on the piston. When a vacuum pressure suitable for mixing is attained in the cylinder, the components are mixed by moving the mixing shaft in and out and simultaneously rotating the mixing shaft, whereby the mixing mechanism processes the components to be mixed into homogeneous flowable bone cement.

After mixing is complete, the mixing shaft is retracted until the mixing mechanism contacts the end face of the piston inside the cylinder, whereafter the mixing shaft is broken off in a region of the mixing shaft positioned outside the cap.

Advantageously, the mixing shaft, when the mixing mechanism is moved completely into a position so as to contact the cylinder-internal end face of the piston, is provided in the region of the outer end face of the piston with a rated break point, where the portion of the mixing shaft positioned outside the piston can be broken off. Due to the tiltable connection of the sealing cap with the locking brackets, the sealing cap can be tilted upwardly, whereby the connection line to the vacuum source is simultaneously pulled off the corresponding suction connection in the piston, venting the interior of the cylinder. After the sealing cap is tilted upwardly, the locking brackets can be pulled out of the recesses in the edge region of the cylinder and through the openings in the piston. The cylinder can then be pushed downwardly, by hand or by using the broken-off mixing shaft, towards the opposing end which is still closed off by a screwed-in sealing plug, thereby compacting the bone cement to a dense mass. The cylinder is then inserted in this condition into a customary application gun, with the piston of this application gun pressed into the end face of the piston on the outside of the cylinder, until contract is established. The sealing plug, which hitherto prevented bone cement from leaking out, is then replaced by an elongated application nozzle, also referred to as "snorkel," and the plastic bone cement mass can be pressed out through the snorkel by operating the application gun. If the application nozzle is used to set up the shaft of an endoprosthesis in the medullary channel of a bone, it should preferably be of sufficient length so as to extend up to the medullary space plug inserted into the medullary space before the shaft of the endoprosthesis is inserted. The bone cement is then filled by operating the application gun to fill the space from the medullary space plug to the open end of the bone, whereby tissue water, blood and other contamination are pushed out by the rising level of the bone cement, leaving only bone cement in these provided space after the shaft of the endoprosthesis has been inserted into the medullary channel filled with bone cement.

The rated break point, which allows the shaft to be easily broken off, is advantageously not disposed on the outside of the mixing shaft, because the required notches could otherwise damage a sealing ring which seals on the mixing shaft.

According to an advantageous embodiment of the invention, the mixing shaft is formed by a small tube having a through-bore extending along its entire length, wherein the rated break point is formed by a circumferentially notched indentation disposed in the interior wall of the small tube.

Advantageously, the vacuum fitting in the piston is formed by a vacuum nipple having a vacuum channel which is guided through the piston into a ring-shaped circumferential recess disposed in the cylinder-side end face of the piston, wherein the ring-shaped circumferential recess is closed off to the inside of the cylinder by a circular porous disk made of a filter material having an average pore size selected to be permeable to gas, but impervious to particles of the powder or granulate component filled in the cylinder and/or to the prepared paste-like mass.

Advantageously, the circular disk made of filter material is held on the cylindrical end face of the piston by a clip ring having a larger diameter and extending over its outer edge and/or by a clip ring having a small diameter and extending over its inner edge.

According to another advantageous embodiment, the clip ring having the larger diameter can include an attachment section that grips over a circumferential section of the piston and has a diameter that is smaller than the unobstructed inside diameter of the cylinder, and/or the clip ring having the smaller diameter can include an attachment section that engages with a bore section having a diameter that is larger than the diameter of the through-opening provided in the piston for the mixing shaft.

A corresponding sealing ring can be disposed in the groove-shaped recesses formed between the clip ring attachment sections and the ring-shaped surfaces produced in the piston in a region where the diameter of the circumferential section or bore section changes, by dimensioning the attachment section of the clip ring that grips over the circumferential section of the piston with the smaller diameter and/or the attachment section of the clip ring that engages with the bore section in the piston with the larger diameter to be shorter in the direction of the longitudinal center axis of the piston than the corresponding circumferential or bore section of the piston. The sealing rings—which can be formed, for example, by O-rings—can be easily mounted, before the clip rings are placed, by pushing or inserting them in the attachment sections disposed in the piston.

Advantageously, the clip rings holding the disk made of filter material on the piston can be attached by interlocking the attachment section of the respective clip ring, which grips over the circumferential section of the piston and/or engages with the corresponding bore section, on or in the associated section of the piston, and/or holding the attachment section with an adhesive and/or by a press fit.

BRIEF DESCRIPTION OF THE DRAWINGS

The invention will be described in more detail in the following description of an embodiment to be read in conjunction with the drawing. It is shown in.

DETAILED DESCRIPTION OF THE INVENTION

Figure 1:
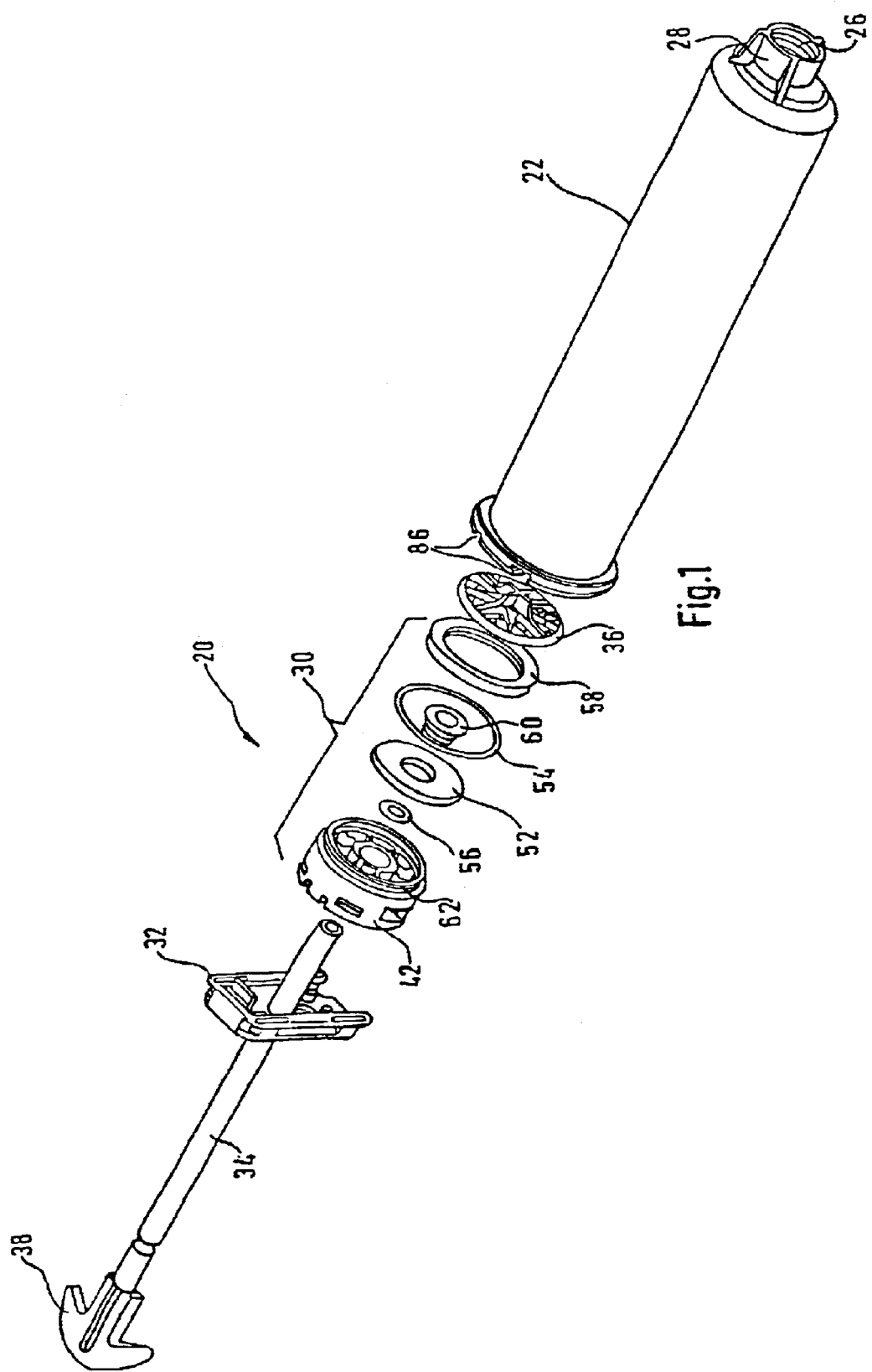
FIG. 1 a perspective exploded view of the device according to the invention.
Figure 2:
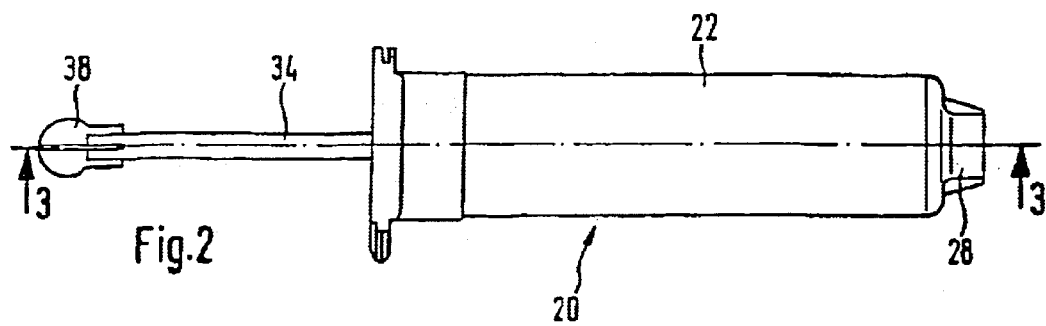
FIG. 2 a side view of the device of FIG. 1.
Figure 3:
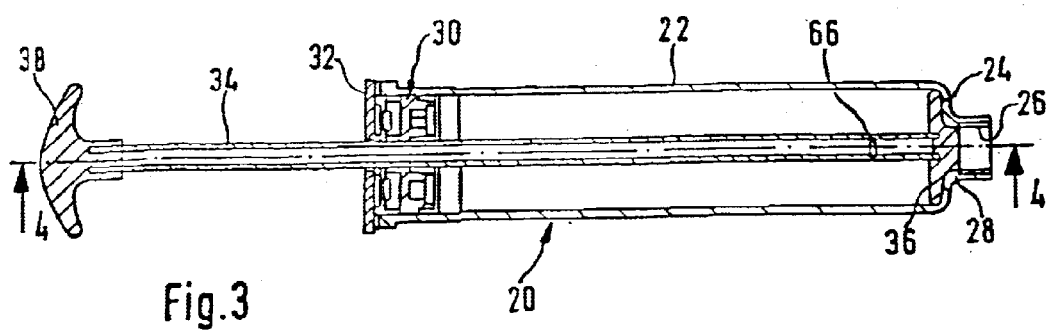
FIG. 3 a side view of the device as viewed in the direction of the arrows 3—3 in FIG. 2.
Figure 4:
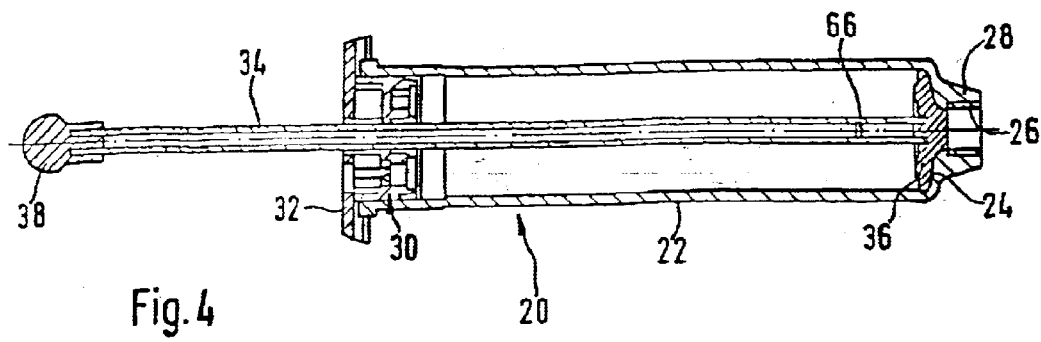
FIG. 4 a side view of the device as viewed in the direction of the arrows 4—4 in FIG. 2.
Figure 5:
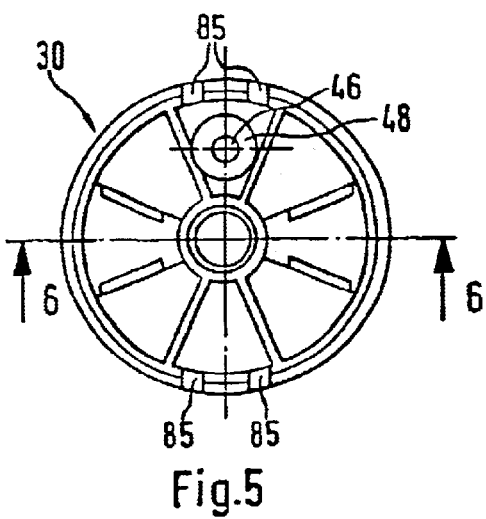
FIG. 5 a top view of the end face of a piston that is movably arranged in a mixing cylinder for pressing out the paste-like mass prepared in the device.
Figure 7:
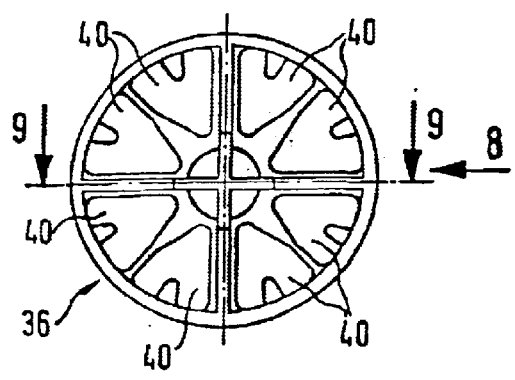
FIG. 7 a bottom view of a mixing mechanism provided in the mixing cylinder and arranged on the end of a mixing shaft inside the cylinder.
Figure 6:
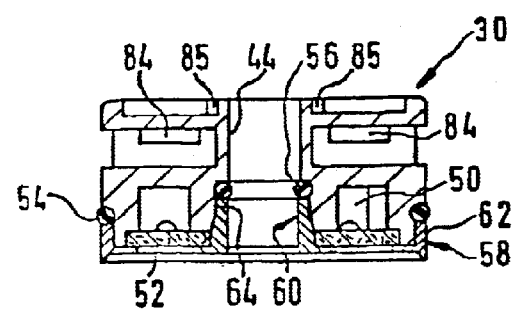
FIG. 6 a cross-sectional view of the piston in a cutting plane depicted by the arrows 6—6 in FIG. 5.
Figure 8:
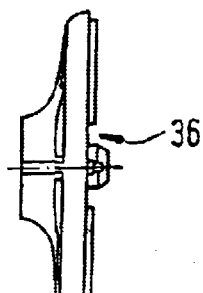
FIG. 8 a side view of the mixing mechanism as viewed in the direction of the arrow 8 in FIG. 7.
Figure 9:
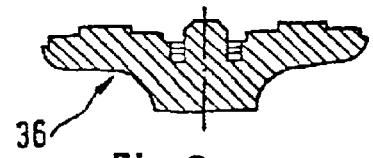
FIG. 9 a cross-sectional view of the mixing mechanism, as viewed in the direction of the arrows 9—9 in FIG. 7.

The device with the reference numeral 20 is illustrated in FIG. 1 in a perspective exploded view and in FIGS. 2 to 4 in a side view in two planes that are offset relative to each other by 90°. The device 20 can be used to mix at least a powder and a liquid component to a paste-like mass, for example bone cement, which can be produced by mixing a polymer powder and a liquid monomer component inside a mixing cylinder 22. The paste-like mass can be inserted after complete mixing—like cartridges containing plastic adhesives or sealing compounds—in a pistol-like application device (not shown), whereby the mass processed in the mixing cylinder can be pressed out of the cylinder 22 and introduced through an elongated application nozzle—sometimes also referred to as "snorkel"—connected to the cylinder into the desired application region, for example the medullary channel of the femur of a patient, with the shaft of a hip replacement endoprosthesis to be affixed in the medullary channel with the bone cement.

The mixing cylinder 22 made of plastic has on the end, which is illustrated in the drawings on the right-hand side, a termination wall 24 with a protruding nipple 28 that is penetrated by a threaded bore 26. This threaded bore 26 is initially sealed by a threaded plug (not shown).

Figure 10:
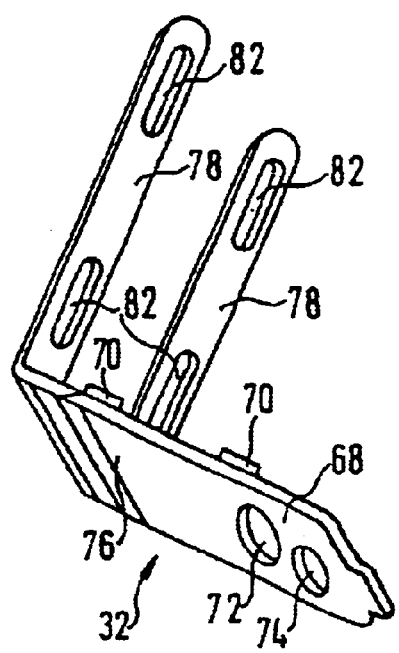
FIG. 10 a perspective view of a sealing cap, which is interlocked together with the piston on the upper open end region of the mixing cylinder after the components to be mixed are introduced into the mixing cylinder.
Figure 12:
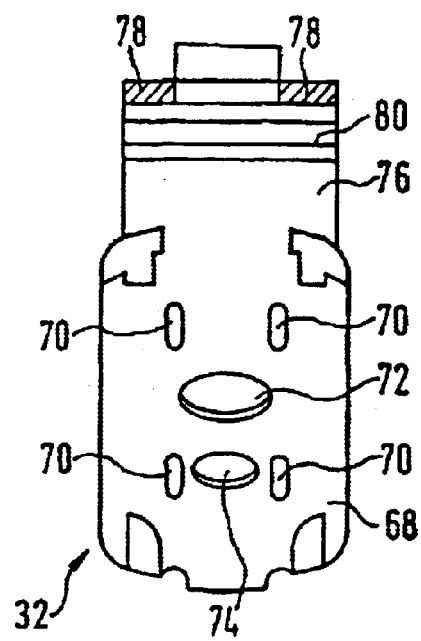
FIG. 12 a cross-sectional view through the sealing cap viewed in the direction of the arrows 12—12 in FIG. 11.
Figure 11:
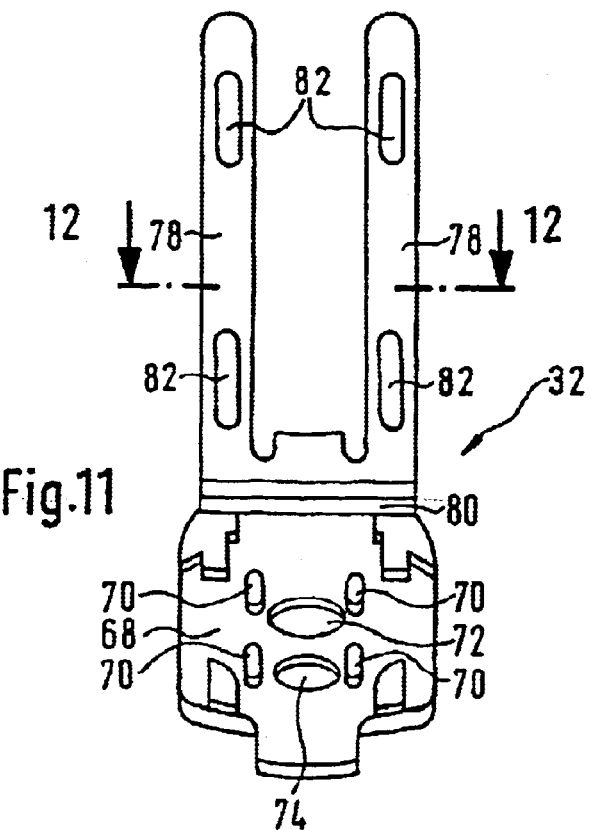
FIG. 11 a view of the sealing cap in the direction of the arrow 11 in FIG. 10.

The components to be mixed can be introduced at the opposite open end of the cylinder 22, whereby this open end can be closed with a sealing cap 32 (FIGS. 10 to 12) connected to a movable piston that can be inserted into the cylinder.

The piston 30 and the sealing cap 32 are penetrated by an elongated mixing shaft 34 that can be moved in the longitudinal direction as well as rotated, whereby the mixing shaft 34 is formed as a hollow small tube and a mixing mechanism 36, also referred to as a "mixing paddle", is attached on the end of the mixing shaft 34 disposed inside the cylinder. A handle 38 is attached to the opposite end outside the cylinder. As seen clearly in FIGS. 3 and 4, the mixing mechanism 40, which is attached at the end of the mixing shaft 34 interior to the cylinder and has a circular boundary and is provided with openings 40, is moveable inside the mixing cylinder 22 over the entire length of the mixing cylinder 22. For example, a person can grip the handle 38 to pull the mixing shaft 34 in and out. The handle 38 can also be rotated by rotating the mixing shaft 34 with the mixing paddle 36 attached thereto.

The piston 30 is comprised of components depicted in FIG. 1 as individual elements, namely the actual cylindrically piston body 42, which has an outside diameter that is substantially identical to the unobstructed inside diameter of the mixing cylinder 22. The piston body 42 has a central through opening 44, through which the mixing shaft 34 is guided. The piston 30 is also penetrated by a continuous vacuum channel 46 which is radially offset from the through opening 44 and terminates on the side facing away from the interior of the cylinder in a vacuum nipple 48 that is recessed in the piston. A line connected with a vacuum source, such as a vacuum pump, can be attached to the vacuum nipple 48 when the components in the mixing cylinder are being mixed. The vacuum channel 46 does not terminate directly in the end face of the piston body inside the cylinder, but in a circumferential annular recess 50, which is closed towards the interior of the cylinder by a ring-shaped porous disk 52 made of a filter material. The porosity of this filter disk 52 is selected so as to be permeable to gas, i.e., both the atmosphere inside the cylinder as well as monomer vapors of the liquid component can be suctioned off through the disk by the vacuum source. Conversely, powder or granular particles of the polymer components are retained inside the cylinder. The processed paste-like mass is also prevented from passing through the filter disk 52.

The piston is sealed in cylinder 22 by an exterior sealing ring 54, which can be formed by an O-ring, whereas the mixing shaft 34 is sealed in the through opening 44 by an interior sealing ring 56 which can also be an O-ring. The sealing rings 54 and 56 are held by corresponding exterior and/or interior clip rings 58, 60 on a peripheral section 62 of the piston body 42 having a correspondingly smaller diameter and/or by a bore section 64 of the through opening 44 in the piston body 42 having a correspondingly larger diameter. The clip rings 58, 60 also grip over the outer and/or inner edges of the filter disk 52, thereby affixing them on the end face of the piston 30 inside the cylinder.

As seen in FIGS. 3 and 4, a rated break point 66 in form of an annular notch in the interior wall of the mixing shaft 34 is disposed at a distance from the mixing paddle 36 on the end of the mixing shaft 34 inside the cylinder. The distance between the rated break point 66 from the mixing mechanism 36 is selected so that the rated break point is approximately aligned with the opposing end face of the piston, i.e., with the end face pointing outwardly from the interior of the cylinder, when the mixing mechanism 36 is completely pulled out to a point where the mixing mechanism contacts the end face of the piston 30 inside the cylinder. In this completely pulled-out state, the mixing shaft 34 can be relativity easily broken off by bending it near the rated break point. The remaining portion of the mixing shaft 34 and the mixing mechanism 36 then remain in a position where the mixing mechanism contacts the piston—held in place by the inner sealing ring 56 with the smaller diameter.

The sealing cap 32 is composed of the actual cover 68 and the wedges 70 interlocking in the piston. The four sealing wedges 70 disposed on the bottom side of the cover engage with the insertion grooves 85 in the piston body 42. A through opening 72 for the mixing shaft and a radially offset additional through opening 74 are provided in the center of the end wall of the cover 68. The vacuum nipple 48 provided in the piston for connection to a line connected with a vacuum source is accessible through opening 74. Two parallel elongated locking brackets are integrally molded on a radial projection 76 of the cover 68 with a film hinge 80. The locking brackets 78 have slot-like openings 82 located proximate to the film hinges 80 and proximate to their free ends, so that the locking brackets 78 can be elastically compressed in the region of the openings 82 in the transverse direction.

The sealing cap 32 and the piston 30 can be connected with each other by aligning the locking brackets 78 approximately parallel with the cover 68 and inserting the locking brackets 78 into openings 84 in the piston 30 that penetrate the piston parallel to its end faces. The regions of the locking brackets 78 having the slot-like openings 82 are thereby located partially inside the openings 84 in the piston and partially in the region of the locking brackets 78 that protrude from the peripheral surface of the piston.

Recesses 86 with a narrowed mouth for receiving the locking brackets 78 are provided near the edge of the open ends of the cylinder, where the locking brackets 78 can engage with the region formed by the elastically compressed slot-like openings 82. Alternatively, the entire assembly formed by the mixing shaft 34 with the attached mixing paddle 36 and handle 38, the piston 30 and the sealing cap 32 pre-mounted in the piston with the locking brackets 78 can be attached to the open end of the mixing cylinder, after the components to be mixed are filled in the interior of the mixing cylinder 22, by inserting the aforedescribed assembly with the mixing paddle 36 first into the open end of the cylinder 22. The piston is subsequently inserted in and pushed into the cylinder until the locking brackets 78 interlock with the edge recesses 86 of the cylinder 22. The four locking wedges 70 disposed on the bottom side of the cover 68 interlock with the corresponding insertion grooves 85 disposed in the edge region of the piston, which holds the sealing cap in the intended mounting position on the mixing cylinder 22. The free end of the line connected to the vacuum source can be pushed through the opening 74 on the vacuum nipple 48 of the vacuum channel 46, allowing the interior space of the cylinder to be evacuated. Once the desired vacuum pressure is reached, the components previously filled into the mixing cylinder 22 are mixed by holding the handle 38 and moving the mixing rod 24 back and forth until the two components are homogeneously mixed.

The mixing rod is then pulled out until the mixing paddle makes contact with the end face of the piston inside the cylinder. Any processed paste-like mass remaining on the end face of the piston or the filter disk 52 can be stripped off by rotating the mixing paddle. The fully extended mixing shaft 24 can then be broken off along the rated break point 66. The cover 68 of the sealing cap 32 can then be pivoted upwardly about the film hinge 80, whereby the free end of the suction line is simultaneously pulled off from the vacuum nipple 48, thereby venting the interior space of the mixing cylinder. This arrangement ensures that the content of the mixing cylinder is compacted and applied only at atmospheric pressure—and never at a reduced pressure. After the cover has been pivoted upwardly, the locking brackets 78 can be pulled out of the openings 84 in the piston and the recesses 86 in the edge region of the mixing cylinder 22. The piston is now positioned in the upper end of the mixing cylinder and freely movable. The piston is then pushed towards the interior of the cylinder—for example with the broken-off part of the mixing shaft—, wherein the processed paste-like mass is compacted to a lump and urged towards the opposite end wall 24 of the mixing cylinder 22 with the threaded opening 26. The plug left in the threaded bore 26 can be exchanged for an elongated tube-like application nozzle, the so-called "snorkel", and the mixing cylinder configured in this way can be inserted in the conventional application gun. The feed piston of this application gun is then moved into contact with the exterior end face of the cylinder, and subsequently moved farther into the interior space of the mixing cylinder by actuating the lever provided on the pistol grip of the application gun. The piston 30 then moves the processed paste-like mass first into the application nozzle and then again out of the application nozzle. In this way, the processed mass, in the present exemplary embodiment the processed bone cement, can be applied with the application nozzle in the application region as intended.

What is claimed is:

1. Preparation and application device (20) for materials which are to be prepared immediately before use as a paste-like, flowable mass from at least one powder or granulate component and one liquid component, especially bone cement, with an elongated mixing cylinder (22) for receiving the components to be mixed, comprising in one end region a sealable through-opening (26) that can optionally be provided with a discharge unit for the paste-like material to be prepared, and a piston (30) which can be inserted into the other, opposite, open end, which piston is displaceable in the cylinder (22) and seals against the inner wall of the cylinder, the piston being penetrated by an elongated mixing shaft (34) sealed against the piston (30), with a mixing mechanism (36) disposed at the cylinder inside-end of the mixing shaft and a handle (38) disposed at the cylinder outside-end of the mixing shaft, wherein the open end of the cylinder (22) located opposite the through-opening (26) and receiving the piston (30) is additionally provided with a removable sealing cap (32) that can be attached to and removed from the cylinder or piston and has a through-opening (72) for the mixing shaft (34), wherein the piston (30) on the side of the sealing cap has a vacuum fitting (48) adapted for connection to a vacuum source, which vacuum source can produce a vacuum in the interior of the cylinder through a passageway provided in the piston, wherein the sealing cap includes a through-opening (74) through which through-opening the vacuum line connected to the vacuum source can be connected to the vacuum fitting in the piston (30), characterized in that the sealing cap (32), which can be placed over the edge of the open end of the cylinder (22), is movably connected to two elongated locking element 78 having flat sides located in a plane which are pre-mounted in a corresponding through-opening (84) of the piston (30), with the through-opening penetrating the piston (30) perpendicular to its longitudinal center axis and being complementary to the cross-section of the locking brackets (78), that in an edge region of the open end of the cylinder (22) there are provided open-ended recesses (86) with a narrowed mouth for receiving the locking brackets (78), and that in the intended locking position of the piston (30) the locking brackets (78) can be elastically pressed together in the transverse direction in the region located at the open end of the cylinder (22) and thereby be inserted in the cylinder (22) through the narrowed mouth of the recesses (86) disposed in the cylinder (22) and openings (84) provided in the piston (30), so as to hold the sealing caps (32) and the cylinder (22) on or in the open end region of the cylinder (22).

2. Device according to claim 1, characterized in that the locking brackets (78) are pivotally joined on the sealing cap (32).

3. Device according to claim 2, characterized in that the sealing cap (32) and the locking bracket(s) (78) are injection molded plastic parts.

4. Device according to claim 3, characterized in that the locking brackets (78) is/are integrally pivotally joined to the sealing cap (32) via a film hinge (80).

5. Device according to claim 1, characterized in that the locking brackets (78) are provided with elongated through-holes (82) disposed in a region that in the intended locking position is located in the recesses (86) of the cylinder (22), which through-holes (82) permit a relative deformation of the remaining edge regions.

6. Device according to claim 1, characterized in that the piston (30), the mixing shaft (34) which movably penetrates the piston (30) and is provided on its cylinder-interior end with the mixing mechanism (36) and on the exterior end with a handle (38), as well as the sealing cap (32) that is penetrated by the mixing shaft (34), together with the latching brackets (78) that are pre-mounted in the through-openings (84) in the piston (30), are pre-mounted in the form of an assembly that can be inserted into the open end of the cylinder (22) and locked by engaging the locking brackets (78) in the recesses (86) disposed in the edge region of the open end of the cylinder (22 ).

7. Device according to claim 6, characterized in that the mixing shaft (34), when the mixing mechanism (36) is moved completely into a position so as to contact the cylinder-internal end face of the piston (30), is provided in the region of the outer end face of the piston (30) with a rated break point (66), along which the portion of the mixing shaft (34) positioned outside the piston (30) can be broken off.

8. Device according to claims 1, characterized in that the mixing shaft (34) is formed by a small tube having a through-bore extending along its entire length, and that the rated break point (66) is formed by a circumferentially notched indentation disposed in the interior wall of the small tube.

9. Device according to claim 8, characterized in that the vacuum fitting in the piston (30) is formed by a vacuum nipple (48) having a vacuum channel (46) which is guided through the piston (30) into a ring-shaped circumferential recess (50) in the cylinder-side end face of the piston (30), and that the ring-shaped circumferential recess (50) is closed off to the inside of the cylinder by a circular porous disk (52) made of a filter material, wherein the average pore size of the filter material is selected so as to be permeable to gas, but impervious to particles of the powder or granulate components filled into the cylinder (22) and/or to the paste-like mass prepared from the components.

10. Device according to claim 9, characterized in that the circular disk (50) made of filter material is held on the cylindrical end face of the piston (30) by a clip ring (58) having a larger diameter and extending over the outer edge of the circular disk (50) and/or by a clip ring (60) having a small diameter and extending over the inner edge of the circular disk (50).

11. Device according to claim 10, characterized in that the clip ring (58) having the larger diameter includes an attachment section that grips over a circumferential section (62) of the piston (30) with a diameter that is smaller than the unobstructed inside diameter of the cylinder (22), and/or the clip ring (60) having the small diameter includes an attachment section that engages with a bore section (64) having a diameter that is larger than the diameter of the through-opening (44) provided in the piston (30) for the mixing shaft (34).

12. Device according to claim 11, characterized in that the attachment section of the respective clip ring (58; 60), which grips over the circumferential section (62) of the piston and/or engages with the bore section (64), interlocks on or in the associated section of the piston (30), and/or is held thereon or therein with an adhesive and/or by a press fit.

13. Device according to claim 10, characterized in that the attachment section of the clip ring (58) gripping over the circumferential section (62) of the piston (30) with the smaller diameter and/or the attachment section of the clip ring (60) engaging with the bore section (64) in the piston (30) having the larger diameter is dimensioned in the direction of the longitudinal center axis of the piston (30) so as to be shorter than the corresponding circumferential or bore section of the piston, and that a corresponding sealing ring (54 and 56, respectively) is disposed in the groove-shaped recesses formed between the clip ring attachment sections and the ring-shaped surfaces formed in the piston in a region where the diameter of the circumferential section or bore section (62 and 64, respectively) changes.

* * * * *